US009364591B2

(12) United States Patent
Hall et al.

(10) Patent No.: US 9,364,591 B2
(45) Date of Patent: Jun. 14, 2016

(54) SYSTEMS AND METHODS FOR MANAGING REDUCED PRESSURE AT A PLURALITY OF WOUND SITES

(75) Inventors: Colin John Hall, Poole (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 1074 days.

(21) Appl. No.: 13/292,926

(22) Filed: Nov. 9, 2011

(65) Prior Publication Data

US 2012/0123358 A1    May 17, 2012

Related U.S. Application Data

(60) Provisional application No. 61/414,718, filed on Nov. 17, 2010.

(51) Int. Cl.
*A61M 1/00* (2006.01)

(52) U.S. Cl.
CPC ........... *A61M 1/0088* (2013.01); *A61M 1/0031* (2013.01); *A61M 1/0027* (2014.02); *A61M 2205/18* (2013.01); *A61M 2205/3344* (2013.01); *A61M 2205/84* (2013.01)

(58) Field of Classification Search
CPC ................ A61M 1/00–1/0098; A61M 1/0236; A61M 27/002–27/008; A61M 31/00; A61B 5/20; A61F 5/44
USPC ......... 604/304, 305, 307, 313, 315, 318, 319, 604/322; 601/7
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report for PCT/US2011/060029 mailed Feb. 23, 2012.

(Continued)

*Primary Examiner* — Jason Flick
*Assistant Examiner* — Ned T Heffner (57) ABSTRACT

Systems and methods are presented for providing reduced pressure to and monitoring pressure at a plurality of tissue sites using a plurality of pressure management devices. The pressure management devices are associated with a plurality of sensing conduits that fluidly couple the pressure management devices and the plurality of tissue sites. Other systems, methods, and devices are disclosed.

18 Claims, 5 Drawing Sheets

(56) References Cited

U.S. PATENT DOCUMENTS

| | | |
|---|---|---|
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0025727 A1* | 2/2006 | Boehringer et al. .......... 604/313 |
| 2007/0265586 A1* | 11/2007 | Joshi et al. .................... 604/313 |
| 2008/0004549 A1 | 1/2008 | Anderson et al. |
| 2008/0041401 A1 | 2/2008 | Casola et al. |
| 2008/0300578 A1* | 12/2008 | Freedman ..................... 604/543 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 10 2006 051223 A1 | 11/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2008/100440 A1 | 8/2008 |
| WO | 2009141820 A1 | 11/2009 |

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastman, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae:"New and Established Methods, *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, "*Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

SYSTEMS AND METHODS FOR MANAGING REDUCED PRESSURE AT A PLURALITY OF WOUND SITES

RELATED APPLICATION

The present invention claims the benefit, under 35 USC §119(e), of the filing of U.S. Provisional Patent Application Ser. No. 61/414,718, entitled "Systems and Methods for Managing Reduced Pressure at a Plurality of Wound Sites," filed 17 Nov. 2010, which is incorporated herein by reference for all purposes.

FIELD

The present disclosure relates generally to medical treatment systems and, more particularly, but not by way of limitation, to systems, devices, and methods for managing reduced pressure at a plurality of wound sites.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, when applied to open wounds, reduced pressure is applied to tissue through a porous pad or other manifold device. The porous pad contains cells or pores that are capable of distributing reduced pressure to the tissue and channeling fluids that are drawn from the tissue. At times, a patient may have a large wound requiring treatment at numerous sites or has a plurality of tissue sites requiring treatment.

SUMMARY

According to some illustrative embodiments, systems and methods are presented for providing reduced pressure to and monitoring pressure at a plurality of tissue sites using a plurality of pressure management devices. The pressure management devices are associated with a plurality of sensing conduits that fluidly couple the pressure management devices and the plurality of tissue sites.

According to an illustrative embodiment, a system for managing reduced pressure at multiple tissue sites undergoing reduced pressure treatment on a patient includes a reduced-pressure source for providing reduced pressure, a plurality of reduced-pressure delivery conduits fluidly coupled to the reduced-pressure source, a plurality of reduced-pressure dressings fluidly coupled to the plurality of reduced-pressure delivery conduits in a one-to-one fashion, a plurality of pressure management devices, and a plurality of a sensing conduits fluidly coupled to the plurality of pressure management devices in a one-to-one fashion. Each reduced-pressure dressing has a sensing conduit of the plurality of sensing conduits and a reduced-pressure delivery conduit of the plurality of reduced-pressure delivery conduits associated with the reduced-pressure dressing. Each pressure management device of the plurality of pressure management devices may include a controller, a power unit electrically coupled to the controller for providing power to the controller, a force transducer associated with a sensing conduit of the plurality of sensing conduits and electrically coupled to the controller for determining if a reduced-pressure threshold exists at a tissue site associated with the sensing conduit, and an indicator coupled to the controller for indicating when insufficient pressure exists in an associated sensing conduit.

According to another illustrative embodiment, a method for managing reduced pressure at a plurality of tissue sites undergoing reduced pressure treatment on a patient includes providing a reduced-pressure source, fluidly coupling a plurality of reduced-pressure delivery conduits to the reduced-pressure source, disposing a plurality of reduced-pressure dressings proximate to the plurality of tissue sites, fluidly coupling the plurality of reduced-pressure dressings to the plurality of reduced-pressure delivery conduits in a one-to-one fashion, providing a plurality of pressure management devices, and fluidly coupling a plurality of a sensing conduits to the plurality of pressure management devices in a one-to-one fashion. Each reduced-pressure dressing has a sensing conduit of the plurality of sensing conduits and a reduced-pressure delivery conduit of the plurality of reduced-pressure delivery conduits associated with the reduced-pressure dressing. Each pressure management device of the plurality of pressure management devices may include a power unit electrically coupled to the controller for providing power to the controller, a force transducer associated with a sensing conduit of the plurality of sensing conduits and electrically coupled to the controller for determining if a reduced-pressure threshold exists at a tissue site associated with the sensing conduit, and an indicator coupled to the controller for indicating when insufficient pressure exists in the associated sensing conduit.

According to another illustrative embodiment, a method of manufacturing a system for managing reduced pressure at multiple tissue sites undergoing reduced pressure treatment on a patient includes providing a reduced-pressure source for providing reduced pressure, providing a plurality of reduced-pressure delivery conduits, fluidly coupling the plurality of reduced-pressure delivery conduits to the reduced-pressure source, providing a plurality of reduced-pressure dressings, providing plurality of pressure management devices, providing a plurality of a sensing conduits, and fluidly coupling the plurality of pressure management devices in a one-to-one fashion to the plurality of sensing conduits. Each reduced-pressure dressing has a sensing conduit of the plurality of sensing conduits and a reduced-pressure delivery conduit of the plurality of reduced-pressure delivery conduits associated with the reduced-pressure dressing. Each pressure management device of the plurality of pressure management devices may include a power unit electrically coupled to the controller for providing power to the controller, a force transducer associated with a sensing conduit of the plurality of sensing conduits and electrically coupled to the controller for determining if a reduced-pressure threshold exists at a tissue site associated with the sensing conduit, and an indicator coupled to the controller for indicating when insufficient pressure exists in an associated sensing conduit.

According to another illustrative embodiment, a system for managing reduced pressure at multiple tissue sites undergoing reduced pressure treatment on a patient includes a reduced-pressure source for providing reduced pressure, a pressure management module, a first conduit fluidly coupled between the reduced-pressure source and the pressure management module, a plurality of reduced-pressure delivery conduits fluidly coupled between the pressure management module and a plurality of reduced-pressure dressings. The plurality of reduced-pressure dressings are coupled to the plurality of reduced-pressure delivery conduits in a one-to-one fashion. The system further includes a plurality of a sensing conduits fluidly coupled to the pressure management module. Each reduced-pressure dressing has a sensing conduit of the plurality of sensing conduits and a reduced-pressure delivery conduit of the plurality of reduced-pressure delivery conduits associated with the reduced-pressure dressing. The pressure management module comprises a plurality of pressure management devices. Each pressure management device of the plurality of pressure management devices may include a power unit electrically coupled to the controller for providing power to the controller, a force transducer associated with a sensing conduit of the plurality of sensing conduits and electrically coupled to the controller for determining if a reduced-pressure threshold exists at a tissue site associated with the sensing conduit, and an indicator coupled to the controller for indicating when insufficient pressure exists in an associated sensing conduit.

According to another illustrative embodiment, a system for managing reduced pressure at multiple tissue sites undergoing reduced pressure treatment on a patient includes a reduced-pressure source for providing reduced pressure and a first plurality of reduced-pressure delivery conduits fluidly coupled to the reduced-pressure source. Each reduced-pressure delivery conduit of the first plurality of reduced-pressure delivery conduits has a first end and a second end. The second end of each of the first plurality of reduced-pressure delivery conduits has a first pressure-management connector coupled thereto. The system further includes a second plurality of reduced-pressure delivery conduits, each having a first end and a second end. The first end of the second plurality of reduced-pressure delivery conduits has a second pressure-management connector. The system further includes a plurality of reduced-pressure dressings fluidly coupled to the second plurality of reduced-pressure delivery conduits in a one-to-one fashion. The first pressure management connector of the plurality of reduced-pressure conduits is coupled to the second pressure-management connector of the second plurality of reduced-pressure in a one-to-one fashion. The first pressure management connector and second management connector couple to form a pressure management device, whereby the first pressure management connectors and the second pressure management connectors form a plurality of pressure management devices. Each reduced-pressure dressing has one of the second reduced-pressure delivery conduits associated with the reduced-pressure dressing. Each pressure management device of the plurality of pressure management devices includes a controller, a power unit electrically coupled to the controller for providing power to the controller, a force transducer associated with a sensing conduit of the first plurality of reduced-pressure conduits and electrically coupled to the controller for determining if a reduced-pressure threshold exists at a tissue site associated with the sensing conduit, and an indicator coupled to the controller for indicating when insufficient pressure exists at the associated sensing conduit.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Reduced pressure provided to tissue sites encourages healing at those tissue sites. To accommodate multiple tissue sites, e.g., multiple wounds on a patient, multiple conduits may be used to deliver reduced pressure. A single reduced pressure source may be used with, the multiple conduits branched off one conduit. Pressure monitoring is currently located in existing reduced-pressure sources and only one conduit communicates pressure to the reduced-pressure source. If only one conduit, which is associated with one tissue site, is monitored, as is the case when monitoring is done at the reduced-pressure source alone, pressure at other tissue sites may be unmonitored. This means that the pressure at the different tissue sites may vary greatly and yet go unnoticed. This, in turn, may cause a detrimental result in some situations. For example, if a graft does not receive reduced pressure for two hours, the graft may not take. With the current system, each tissue site of the plurality of tissue sites is monitored, and issues with reduced pressure delivery may be identified and addressed. An illustrative embodiment of a system 100 is presented that includes, among other things, pressure monitoring at multiple tissue sites.

Figure 1:
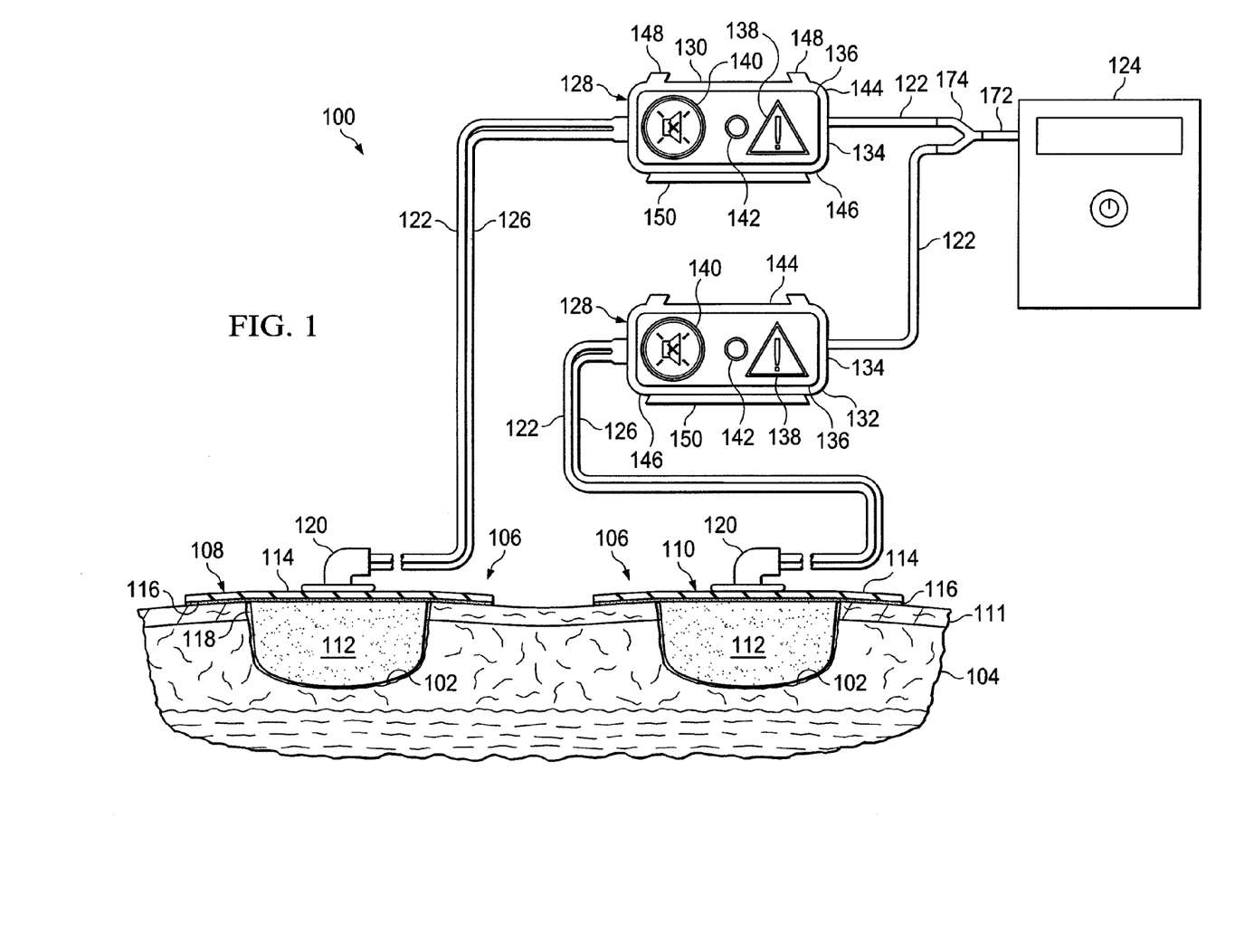
FIG. 1 is a schematic diagram, with a portion shown in cross section, of an illustrative, non-limiting embodiment of a system for managing reduced pressure at multiple tissue sites undergoing reduced pressure treatment on a patient.

Referring now to the drawings and initially to FIG. 1, the system 100 for managing reduced pressure at a plurality of tissue sites 102 that are undergoing reduced pressure treatment on a patient 104 is presented. A plurality of reduced-pressure dressings 106 are used with the plurality of tissue sites 102. Typically, one of the plurality of reduced-pressure dressings 106 is associated with one of the plurality of tissue sites 102. The tissue sites 102 may comprise a single extended tissue site or wound or may be discrete wound sites or tissue sites. Each of the tissue sites 102 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used throughout this document, "or" does not require mutual exclusivity. Treatment of the tissue sites 102 may include removal of fluids, e.g., exudate or ascites.

The plurality of reduced-pressure dressings 106 in the illustrative embodiment of FIG. 1 is shown with a first reduced-pressure dressing 108 and a second reduced-pressure dressing 110. The plurality of reduced-pressure dressings 106 may include any structure suitable for providing reduced pressure to a tissue site and removing fluids. For example, in one illustrative embodiment, the first reduced-pressure dressing 108 includes a manifold 112 that is disposed proximate to one of the tissue sites 102 with which the manifold 112 is associated. The manifold 112 is covered with a sealing member 114, which may include an attachment device 116, that creates a fluid seal. A fluid seal is a seal adequate to maintain reduced pressure at a desired tissue site given the particular reduced-pressure source or subsystem involved. The sealing member 114, which may include the attachment device 116, creates a sealed space 118 in which the manifold 112 may reside. A reduced-pressure interface 120 may be placed through an aperture (not shown) and the sealing member 114 to provide reduced pressure into the sealed space 118 and in particular to the manifold 112. For example, the reduced pressure interface 120 may be a T.R.A.C.® Pad or Sensa T.R.A.C.® Pad available from KCI of San Antonio, Tex. The reduced-pressure interface 120 delivers the reduced pressure to the sealed space 118. The second reduced-pressure dressing 110 is analogous to the first reduced-pressure dressing 108.

With respect to the manifold 112, a manifold is generally a substance or structure that is provided to assist in applying reduced pressure to, delivering fluids to, or removing fluids from a tissue site, e.g., tissue site 102. The manifold 112 typically includes a plurality of flow channels or pathways that distribute fluids provided to and removed from the tissue site 102 around the manifold 112. In one illustrative embodiment, the flow channels or pathways are interconnected to improve distribution of fluids provided or removed from the tissue site 102. The manifold 112 comprises one or more of the following: a biocompatible material that is capable of being placed in contact with the tissue site 102 and distributing reduced pressure to the tissue site 102; devices that have structural elements arranged to form flow channels, such as, for example, cellular foam, open-cell foam, porous tissue collections, liquids, gels, and foams that include, or cure to include, flow channels; material that may be porous and may be made from foam, gauze, felted mat, or any other material suited to a particular biological application; foam with interconnected cells; polyurethane; open-cell, reticulated foam such as GranuFoam® material manufactured by Kinetic Concepts, Incorporated of San Antonio, Tex.; bioresorbable material; or scaffold material. In some situations, the manifold 112 may also be used to distribute fluids such as medications, antibacterials, growth factors, and various solutions to the tissue site 102. Other layers may be included in or on the manifold 112, such as absorptive materials, wicking materials, hydrophobic materials, and hydrophilic materials.

In one illustrative embodiment, the manifold 112 may be constructed from bioresorbable materials that do not have to be removed from a patient's body following use of the reduced-pressure dressing 108, 110. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 112 may further serve as a scaffold for new cell-growth, or a scaffold material may be used in conjunction with the manifold 112 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The sealing member 114 may be any material that provides a fluid seal. The sealing member 114 may, for example, be an impermeable or semi-permeable, elastomeric material. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, 3M Tegaderm® drape, polyurethane (PU) drape such as one available from Avery Dennison Corporation of Pasadena, Calif.

The attachment device 116 may be used to hold the sealing member 114 against the patient's epidermis 111 or another layer, such as a gasket or additional sealing member, or another location. The attachment device 116 may take numerous forms. For example, the attachment device 116 may be a medically acceptable, pressure-sensitive adhesive that extends about a periphery of the sealing member 114.

The reduced-pressure dressings 106 provide reduced pressure to the tissue sites 102. Reduced pressure is generally a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

A plurality of reduced-pressure delivery conduits 122 may be fluidly coupled to a reduced-pressure source 124. The reduced-pressure delivery conduits 122 may be conduits for carrying reduced pressure and removing liquids alone or may be combined with one or more lumens for sensing pressure and providing a vent or a purge. For description purposes, a distinct plurality of sensing conduits 126, or lumens, is shown associated with the plurality of reduced-pressure delivery conduits 122, but it should be understood that the sensing conduits 126 may be incorporated into the plurality of reduced-pressure delivery conduits 122 as a lumen in a multilumen conduit.

The reduced-pressure source 124 provides reduced pressure. The reduced-pressure source 124 may be any device or source for supplying a reduced pressure, such as a vacuum pump, wall suction, micro-pump, or other source. If the reduced-pressure source 124 is a micro-pump, the micro-pump may be directly coupled to the plurality of management devices 128. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

The plurality of pressure management devices 128 may be coupled to the plurality of reduced-pressure delivery conduits 122 and fluidly coupled to the plurality of sensing conduits 126. The plurality of pressure management devices 128 may include, for example, a first pressure management device 130 and a second pressure management device 132. Each of the plurality of pressure management devices 128 may include a housing 134. The housing 134 may include a visual indicator 136 that may include indicators such as pressure disruption or caution symbol 138 and a touch mute button 140. A manual power switch 142 may also be included on the housing 134 or on the visual indicator 136. Each housing 134 may include a first portion 144 and a second portion 146 or edge. A first coupling member 148, which may include two components, may be coupled to the first portion 144. A second coupling member 150 may be formed on the second portion 146. The first coupling member 148 and the second coupling member 150 are sized and configured to couple with one another either fixedley or releasably. As described further below in connection with FIG. 3, the optional coupling members 148, 150 allow the plurality of pressure management devices 128 to be combined to form an integral module, i.e., a single unit. Other techniques and devices, e.g., fasteners or clips, may be used to couple the pressure management devices 128.

Figure 2:
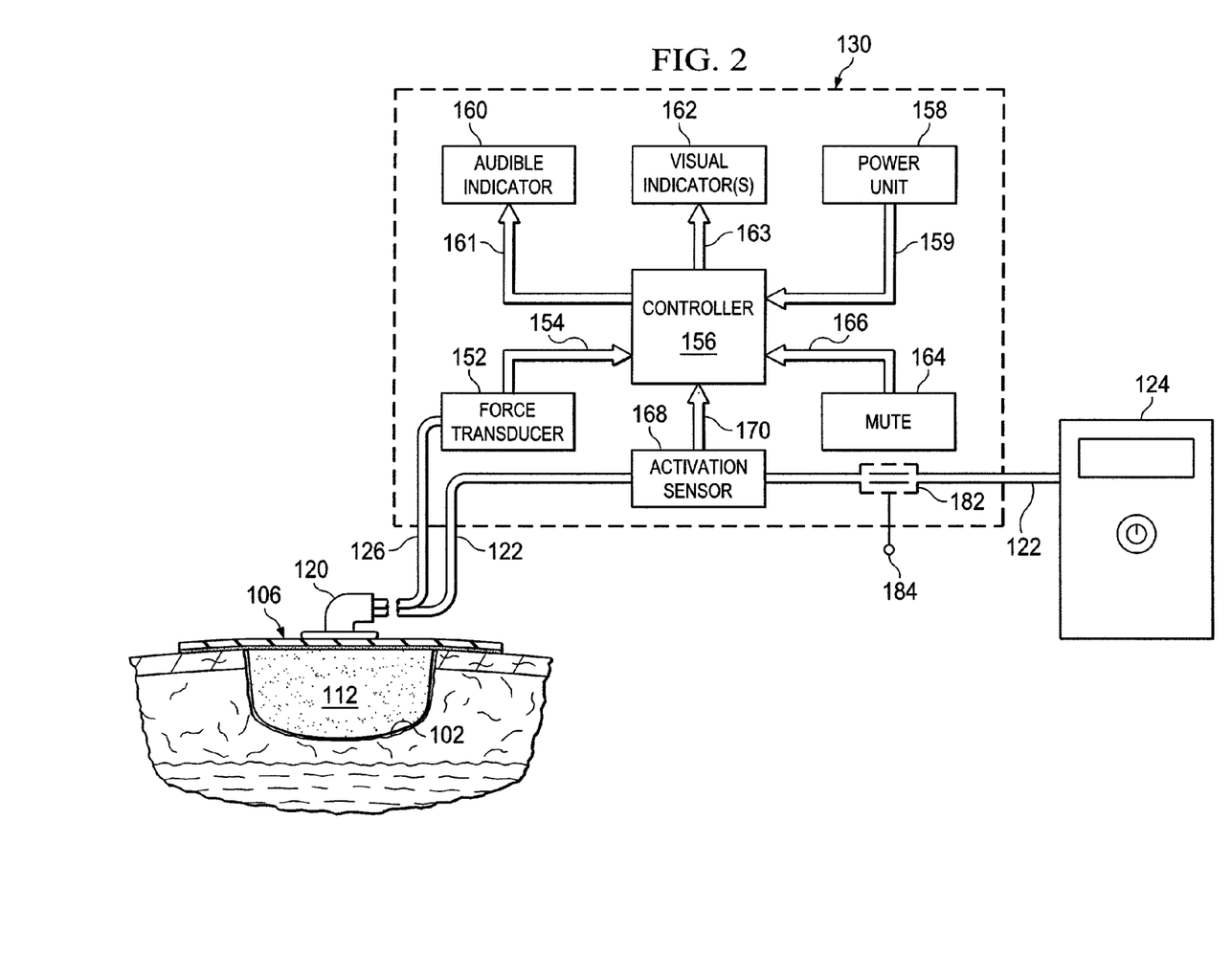
FIG. 2 is a schematic diagram of a portion of an illustrative embodiment of a system for managing reduced pressure at multiple tissue sites undergoing reduced pressure treatment on a patient showing an illustrative, non-limiting configuration of a pressure management device.

Referring now primarily to FIG. 2, the system 100 for managing reduced pressure at the plurality of tissue sites 102 is presented in diagram form with only the first pressure management device 130 of the plurality of pressure management devices 128 shown. It should be understood that any number of additional pressure management devices 128 may be combined as part of the system 100. Additional aspects of the first pressure management device 130 may be explained in more detail with reference to FIG. 2.

The first pressure management device 130 is fluidly coupled to one of the plurality of sensing conduits 126, and the sensing conduit 126 is fluidly coupled to a force transducer 152 (or pressure gauge) within the first pressure management device 130. The force transducer 152 is able to develop a signal, e.g., an electrical signal, that indicates the pressure within the sensing conduit 126 or is otherwise able to detect various thresholds of pressure. The force transducer 152 is coupled at 154 to a controller 156. The controller 156 may be a printed wire assembly (PWA) or an application specific integrated circuit (ASIC), a microprocessor with associated memory, or other controller device.

The controller 156 is able to thus monitor the pressure within the sensing conduit 126 and thereby to monitor pressure proximate to the tissue site 102. The controller 156 receives power from a power unit 158, such as a battery or other source of electrical power. The power unit 158 is coupled at 159 to the controller 156. When the controller 156 determines that the reduced pressure within the sensing conduit 126 is inadequate (e.g., below a reduced-pressure threshold), such as may be caused by a leak in the reduced-pressure dressing associated with the particular sensing conduit 126 or a blockage or other problem, the controller 156 may activate or modify an indicator, such as an audible indicator 160 (or alarm) or a visual indicator 162. The audible indicator 160 is shown coupled at 161 to the controller 156. The visual indicator 162 is shown coupled at 163 to the controller 156. A mute switch or button 164 may be associated with the controller 156 and is shown coupled at 166. The mute switch 164 may allow a user to silence the audible indicator 160. Other user interfaces may be coupled to the controller 156 to control other aspects of the first pressure management device 130.

A portion of the reduced-pressure delivery conduit 122 may extend through the first pressure management device 130, and an activation sensor or transducer 168 may be fluidly coupled to the reduced-pressure delivery conduit 122. The activation sensor 168 can detect the presence of reduced pressure and provide a signal 170 to the controller 156. The controller 156 may compare the pressure delivered through the reduced-pressure delivery conduit 122 with the sensing pressure in the sensing conduit 126 to make certain determinations concerning performance and may also use the signal from the activation sensor 168 to continue to run controller 156 and other aspects of the first pressure management device 130.

Referring now primarily to FIGS. 1 and 2, in operation, according to one illustrative embodiment, a user may apply the plurality of reduced-pressure dressings 106 to the plurality of tissue sites 102. For example, the manifold 112 of the first reduced-pressure dressing 108 may be placed against the tissue site 102 and then be covered by the sealing member 114 to create the sealed space 118. A reduced pressure interface 120, if not already installed, may be installed to provide reduced pressure to the sealed space 118 or otherwise to the manifold 112. Other reduced-pressure dressings may be applied to each tissue site 102 for which treatment is desired.

The plurality of reduced-pressure delivery conduits 122 may be fluidly coupled to the reduced-pressure source 124 in a one-to-one fashion. In this regard, the reduced-pressure source 124 may have a first conduit 172 (FIG. 1) that goes to a branching member or splitter 174 that fluidly couples the plurality of reduced-pressure delivery conduits 122 to the reduced-pressure source 124. The plurality of sensing conduits 126 are fluidly coupled to the plurality of pressure management devices 128.

The reduced-pressure source 124 is activated and begins to deliver reduced pressure to the plurality of reduced-pressure dressings 106. The plurality of pressure management devices 128 may be activated either automatically by the activation sensors 168 or manually by the user using an interface such as power switch 142. Thus, reduced pressure is delivered to the tissue sites 102 and is monitored for each tissue site 102. If there is a problem with the reduced pressure delivery at a tissue site 102 as sensed by one of the plurality of sensing conduits 126, the pressure management device 128 associated with that particular sensing conduit of the plurality of sensing conduits 126 will sense the inadequate pressure via the associated force transducer 152. The controller 156, which monitors the force transducer 152, will then provide an indication using the audible indicator 160 or the visual indicator 162. The user may then identify which reduced-pressure dressing of the plurality of reduced-pressure dressings 106 is having the difficulty. Corrective action may then be readily taken.

Figure 3:
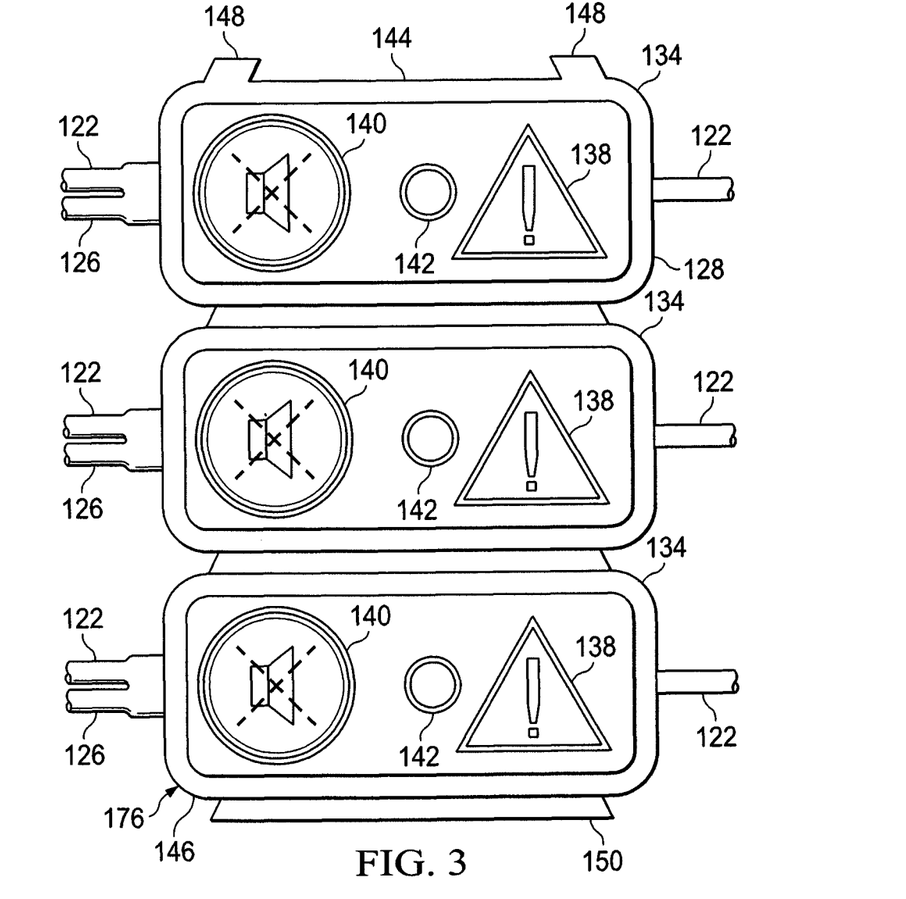
FIG. 3 is a schematic, elevation view of an illustrative embodiment of an integral module formed from a plurality of pressure management devices.

As shown in FIG. 3, the plurality of pressure management devices 128 may be coupled using the first coupling members 148 and the second coupling members 150 to form an integral module 176. The integral module 176 provides for more convenient movement by the user and may also be more aesthetic.

Figure 4:
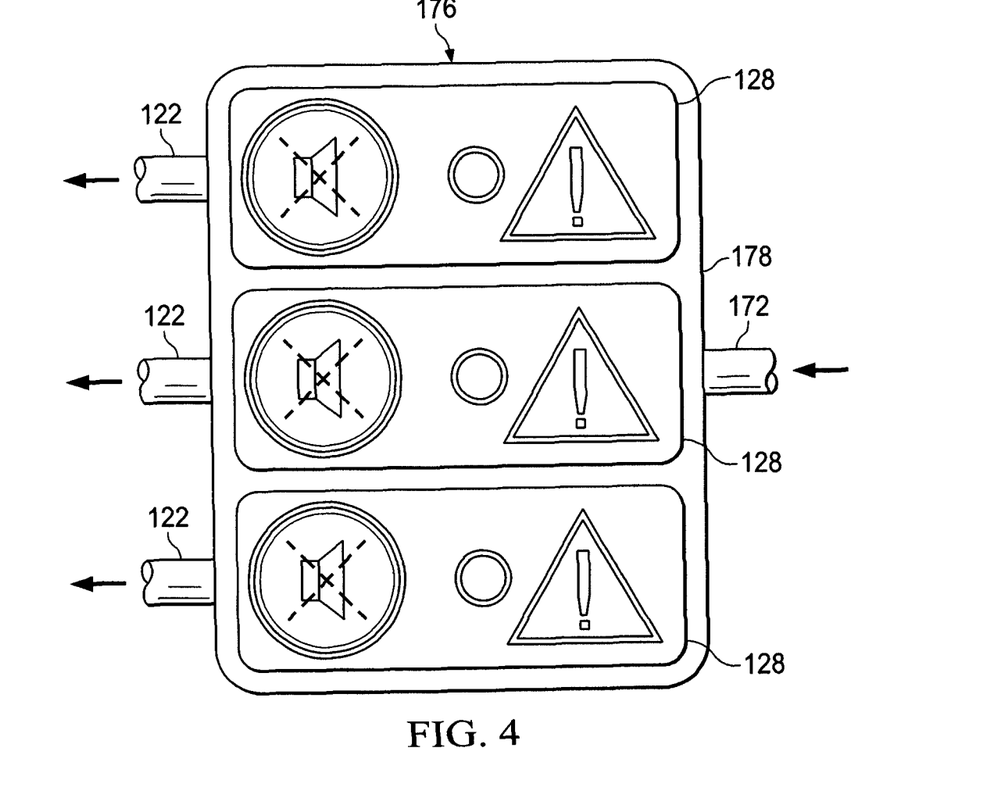
FIG. 4 is a schematic, elevation view of an illustrative embodiment of an integral module that involves a conduit delivering reduced pressure that is split to provide reduced pressure to a plurality of reduced-pressure delivery conduits.

Referring now primarily to FIG. 4, an illustrative embodiment of an integral module 176 or pressure management module 176 is presented that is analogous in most respects to the integrated module 176 shown in FIG. 3. Accordingly, some parts are labeled but not further described here. There are, however, two main differences. First, the integrated module 176 of FIG. 4 may be manufactured with three otherwise independent pressure management devices is a single housing 178. Second, and related, the integrated pressure management module 176 functions as a junction or branching member or splitter to receive reduced pressure from a first conduit 172 from a reduced-pressure source and to provide reduced pressure to each of the plurality of pressure management devices 128 for delivery through a plurality of reduced-pressure delivery conduits 122. While not explicitly shown, associated with or formed as part of the reduced-pressure delivery conduits 122 is a plurality of pressure sensing lumens or conduits. The plurality of sensing lumens allows the plurality of pressure management devices to monitor pressure at a plurality of tissue sites. At least one reduced-pressure delivery conduit 122 may be a sensing lumen that provides pressure for sensing purposes to the reduced-pressure source, e.g., reduced-pressure source 124 in FIG. 1.

Referring again primarily to FIG. 2, another illustrative embodiment of system 100 will be presented. With respect to this embodiment of system 100, the reduced pressure delivered by reduced-pressure source 124 may be at a reduced pressure greater (more negative on an absolute pressure scale) than required anywhere in the system 100 and then stepped down to the desired pressure at various locations. Thus, as an aspect of each of the plurality of pressure management devices 128, a pressure regulating valve 182 may be provided to adjust the reduced pressure delivered from the reduced-pressure source 124 to the specific pressure desired for a particular tissue site 102 associated with that particular pressure management device.

The pressure regulating valve 182 may have an adjustment control 184 for setting the desired pressure. Thus, as one example, a single reduced-pressure source 124 may be used that provides relatively higher reduced pressure (for example, but not by way of limitation, −200 mm Hg) and then adjusted by the pressure regulating valve 182 to a first desired pressure (e.g., but not by way of limitation, to −150 mm Hg) and delivered to a tissue site from which a graft has been taken. The system 100 also provides reduced pressure to a reduced-pressure dressing at the tissue site where the graft has been placed and may do so at a second desired pressure that is relatively less than the first desired pressure (e.g., but not by way of limitation, −50 mm Hg). In another illustrative embodiment, the controller 156 may control the adjustment control 184. The desired pressure may be set by a user using a user interface to the controller 156.

Figure 5:
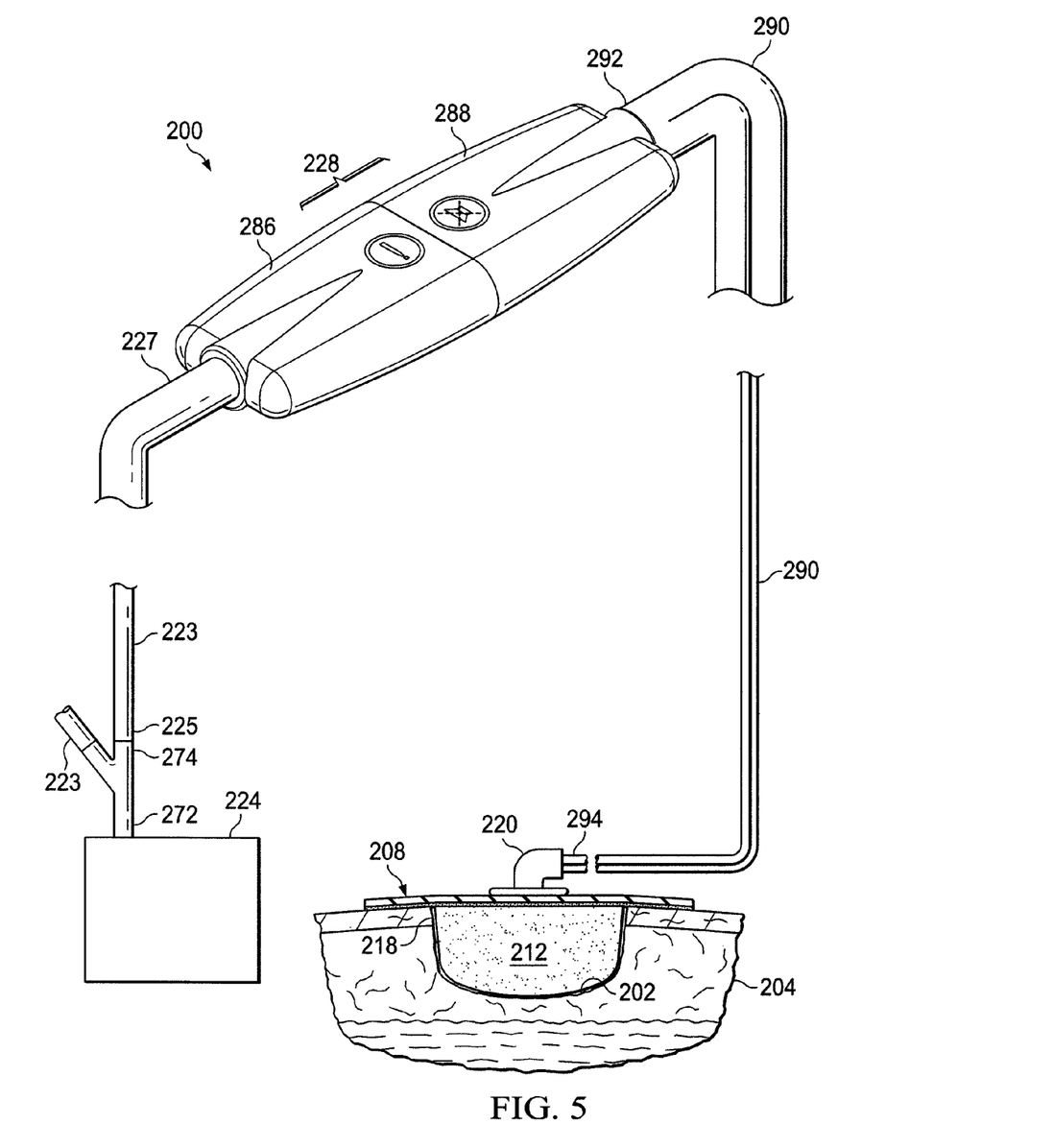
FIG. 5 is a schematic, perspective view, with a portion shown as a diagram and a portion as a cross section, of another illustrative embodiment of a portion of a system for managing reduced pressure at multiple tissue sites undergoing reduced pressure treatment on a patient.

Referring now primarily to FIG. 5, an illustrative, non-limiting system 200 for managing reduced pressure at a plurality of tissue sites, e.g., tissue site 202, undergoing reduced pressure treatment on a patient 204 is presented. The system 200 is analogous in many respects to the system 100 of FIG. 1. While only one reduced-pressure dressing 208 and one pressure management device 228 is shown, it should be understand that the system 200 contemplates a plurality of each. The plurality of reduced-pressure dressings, such as reduced pressure dressing 208, is placed on the tissue sites, e.g., tissue site 202. With each reduced-pressure dressing, a reduced-pressure interface 220 may be used to provide reduced pressure to a sealed space 218 that contains a manifold 212 and also allows for sensing of the pressure in the sealed space 218.

A reduced-pressure source 224 delivers reduced pressure to a first plurality of reduced-pressure delivery conduits 223. A first conduit 272 may be used to deliver the reduced pressure to one or more splitters 274 or distributors that are fluidly coupled to the first plurality of reduced-pressure delivery conduits 223. Each of the first reduced-pressure delivery conduits 223 has a first end 225 and a second end 227. Coupled to the second end 227 of each of the first reduced-pressure delivery conduits 223 is a first pressure management connector 286. A second pressure management connector 288 is releasably coupled to the first pressure management connector 286 to form a pressure management device 228. A second plurality of reduced-pressure delivery conduits 290 may be used to fluidly couple the reduced-pressure interface 220 to the associated second pressure management connector 288 for each reduced-pressure dressing. Each of the second plurality of reduced-pressure delivery conduits 290 has a first end 292 and a second end 294. The second pressure management connector 288 is coupled to the first end 292 of the associated conduit of the second plurality of reduced-pressure conduits 290.

Each pressure management device 228 created by coupling the first pressure management connector 286 and the second pressure management connector 288 provides both a fluid coupling and may also function analogously to the pressure management devices 128 of FIGS. 1-3 with respect to monitoring and control. The pressure management devices 228 provide a quick connection and also readily allow for one portion, e.g., the first pressure management connector 286, to be reused and for another portion, e.g., the second pressure management connector 288, to be discarded after use. Physically coupling the connectors 286, 288 may also provide an electrical connection between the connectors 286, 288. Referring back to FIG. 2 again, various components of the first pressure management device 130 may be associated with either of the connectors 286, 288 of the pressure management device 228.

In one illustrative embodiment, the audible indicator 160 and visual indicator 162 may be associated with the first pressure management connector 286. The controller 156, power unit 158, mute switch 164, and force transducer 152 may be associated with the second pressure management connector 288. Various combinations and permutations of the components may be associated with the two connectors 286, 288. The pressure regulating valve 182 may also be associated with the second pressure management connector 288.

As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid may be in communication between the designated parts or locations.

In another illustrative embodiment, the pressure management device may have no electronics and may use a physical device to monitor pressure and to indicate inadequate pressure. For example, a pop-up pressure valve may be associated with each sensing lumen that is compressed under adequate reduced pressure, but expands and is visible when inadequate reduced pressure exists.

The pressure management devices 128 may be used with any reduced-pressure source, which may be any device for supplying a reduced pressure, such as a vacuum pump, wall suction, or other source. With the inclusion of a pressure regulating valve 182, the pressure management devices 128 allow for a single reduced-pressure source to supply and monitor reduced pressure at different pressures at different tissue sites.

The reduced-pressure source may be a monitored system that monitors one tissue site from which one conduit is fluidly coupled, and the pressure management devices may be added to the additional conduits associated with additional tissue sites.

Referring again generally to FIGS. 1 and 4, in another illustrative embodiment, a system 100 for managing reduced pressure at a plurality of tissue sites 102 that are undergoing reduced pressure treatment on a patient 104 is presented. In this illustrative embodiment, an integral module 176 has a plurality of pressure management devices 128 similar to those presented in FIG. 4, but with only one controller (not explicitly shown) for the integral module 176. The force transducers associated with each pressure management device 128 are coupled to the one controller for the integral module 176.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for managing reduced pressure at a plurality of tissue sites undergoing reduced pressure treatment on a patient, the system comprising:
   a reduced-pressure source for providing reduced pressure;
   a plurality of reduced-pressure delivery conduits fluidly coupled to the reduced-pressure source;
   a plurality of reduced-pressure dressings fluidly coupled to the plurality of reduced-pressure delivery conduits in a one-to-one fashion;
   a plurality of pressure management devices;
   a plurality of sensing conduits fluidly coupled to the plurality of pressure management devices in a one-to-one fashion;
   wherein each reduced-pressure dressing has a sensing conduit of the plurality of sensing conduits associated with the reduced-pressure dressing; and
   wherein each pressure management device of the plurality of pressure management devices comprises:
   a housing, the housing of at least one of the pressure management devices configured to be coupled in direct contact with the housing of another of the pressure management devices;
   a controller positioned in the housing,
   a power unit positioned in the housing and electrically coupled to the controller for providing power to the controller,
   an activation sensor configured to run the controller upon detecting reduced pressure,
   a force transducer positioned in the housing and associated with a sensing conduit of the plurality of sensing conduits and electrically coupled to the controller for determining if a reduced-pressure threshold exists at a tissue site associated with the sensing conduit, and
   an indicator positioned on the housing and coupled to the controller for indicating when insufficient pressure exists in an associated sensing conduit.

2. The system of claim 1, wherein the activation sensor is fluidly coupled to a reduced-pressure delivery conduit associated with the pressure management device and electrically coupled to the controller.

3. The system of claim 1, wherein the indicator is selected from the group of an audible indicator and a visual indicator.

4. The system of claim 1, wherein each pressure management device further comprises a muting switch.

5. The system of claim 1, wherein the plurality of pressure management devices are coupled to form an integral module.

6. The system of claim 1, wherein each of the plurality of reduced-pressure dressings comprises: a manifold for placing proximate to the tissue site, a sealing member for covering the manifold and tissue site to create a sealed space, and a reduced-pressure interface for providing reduced pressure to the sealed space.

7. The system of claim 1, wherein each of the plurality of pressure management devices comprises:
   a first coupling member coupled to a first portion of the housing,
   a second coupling member coupled to a second portion of the housing, and
   wherein the first coupling member is sized and configured to couple with the second coupling member on another of the plurality of pressure management devices, whereby adjacent pressure management devices may be coupled.

8. A method for managing reduced pressure at a plurality of tissue sites undergoing reduced pressure treatment on a patient, the method comprising:
   providing a reduced-pressure source;
   fluidly coupling a plurality of reduced-pressure delivery conduits to the reduced-pressure source;
   disposing a plurality of reduced-pressure dressings proximate to the plurality of tissue sites;
   fluidly coupling the plurality of reduced-pressure dressings to the plurality of reduced-pressure delivery conduits;
   providing a plurality of pressure management devices for monitoring pressure, each of the pressure management devices comprising a housing and being configured to be automatically activated upon detecting reduced pressure;
   coupling the housing of at least one of the pressure management devices in direct contact with the housing of another of the pressure management devices;

fluidly coupling a plurality of a sensing conduits to the plurality of pressure management devices in a one-to-one fashion; and wherein each reduced-pressure dressing has a sensing conduit of the plurality of sensing conduits associated with the reduced-pressure dressing.

9. The method of claim 8, further comprising coupling the plurality of pressure management devices together to form an integral module.

10. The method of claim 8, wherein each of the plurality of reduced-pressure dressings comprises: a manifold for placing proximate to the tissue site, a sealing member for covering the manifold and tissue site to create a sealed space, and a reduced-pressure interface for providing reduced pressure to the sealed space.

11. The method of claim 8, wherein each pressure management device of the plurality of pressure management devices comprises:
a controller,
a power unit electrically coupled to the controller for providing power to the controller,
a force transducer associated with a sensing conduit of the plurality of sensing conduits and electrically coupled to the controller for determining if a reduced-pressure threshold exists at a tissue site associated with the sensing conduit, and
an indicator coupled to the controller for indicating when insufficient pressure exists in an associated sensing conduit.

12. The method of claim 11, wherein each pressure management device further comprises an activation sensor fluidly coupled to a reduced-pressure delivery conduit associated with the pressure management device and electrically coupled to the controller, the activation sensor configured to run the controller and to activate the pressure management device upon detecting reduced pressure in the reduced-pressure delivery conduit.

13. The method of claim 11, wherein the indicator is selected from the group of an audible indicator and a visual indicator.

14. The method of claim 11, wherein each pressure management device further comprises a muting switch.

15. A system for managing reduced pressure at a plurality of tissue sites undergoing reduced pressure treatment on a patient, the system comprising:
a reduced-pressure source for providing reduced pressure;
a pressure management module comprising a plurality of pressure management devices, each pressure management device including a housing, the housing of at least one of the pressure management devices configured to be coupled in direct contact with the housing of another of the pressure management devices;
a first conduit fluidly coupled between the reduced-pressure source and the pressure management module for supplying reduced pressure to the pressure management module;
a plurality of reduced-pressure dressings;
a plurality of reduced-pressure delivery conduits fluidly coupled to the pressure management module;
wherein the plurality of reduced-pressure dressings are coupled to the plurality of reduced-pressure delivery conduits;
a plurality of sensing conduits fluidly coupled to the pressure management module; and
wherein each reduced-pressure dressing has a sensing conduit of the plurality of sensing conduits associated with the reduced-pressure dressing.

16. The system of claim 15, wherein each pressure management device of the plurality of pressure management devices comprises:
a controller,
a power unit electrically coupled to the controller for providing power to the controller,
a force transducer associated with a sensing conduit of the plurality of sensing conduits and electrically coupled to the controller for determining if a reduced-pressure threshold exists at a tissue site associated with the sensing conduit, and
an indicator coupled to the controller for indicating when insufficient pressure exists in an associated sensing conduit.

17. The system of claim 15, wherein each pressure management device further comprises an activation sensor fluidly coupled to the first conduit and electrically coupled to the controller, the activation sensor configured to activate the pressure management device upon detecting reduced pressure in the first conduit.

18. The system of claim 15, wherein the indicator is selected from the group of an audible indicator and a visual indicator.

* * * * *